United States Patent [19]

Autissier et al.

[11] 4,364,939
[45] Dec. 21, 1982

[54] DERIVATIVES OF COENZYME $B_{12}$

[75] Inventors: Denise Autissier, Paris; Pierre Barthelemy, Barbery, both of France

[73] Assignee: Roussel Uclaf, Paris, France

[21] Appl. No.: 186,831

[22] Filed: Sep. 15, 1980

Related U.S. Application Data

[63] Continuation-in-part of Ser. No. 38,774, May 14, 1979, abandoned, which is a continuation of Ser. No. 852,036, Nov. 16, 1977, abandoned.

[30] Foreign Application Priority Data

Nov. 25, 1976 [FR] France .................................. 76 35533

[51] Int. Cl.³ ...................... A61K 31/52; C07H 19/18
[52] U.S. Cl. ..................................... 424/180; 424/201; 536/25
[58] Field of Search ................ 544/225; 424/245, 201, 424/180; 536/25

[56] References Cited

U.S. PATENT DOCUMENTS

| | | | |
|---|---|---|---|
| 3,095,413 | 6/1963 | Sasse et al. ............................ | 544/225 |
| 3,151,116 | 9/1964 | de Stevens et al. .................. | 544/225 |
| 3,213,082 | 10/1965 | Smith et al. ............................ | 536/25 |
| 3,573,276 | 3/1971 | Wagner ................................ | 424/201 |

Primary Examiner—Nicholas S. Rizzo
Attorney, Agent, or Firm—Hammond & Littell, Weissenberger and Muserlian

[57] ABSTRACT

Novel monoesters of cobamide derivatives of coenzyme $B_{12}$ of the formula:

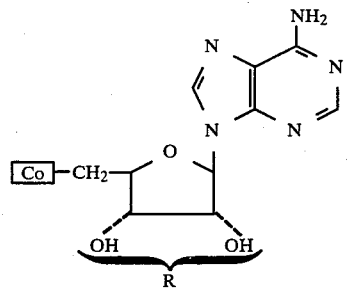

wherein R is acyl of an organic carboxylic acid of 4 to 20 carbon atoms and [Co] is α-(5,6-dimethyl-benzimidazolyl)-cobamide which is a mixture of the said monoesters having dibencozide type properties and a process for their preparation.

14 Claims, No Drawings

DERIVATIVES OF COENZYME $B_{12}$

PRIOR APPLICATION

This application is a continuation-in-part of our copending U.S. patent application Ser. No. 038,774 filed May 14, 1979, now abandoned, which in turn is a continuation of copending application Ser. No. 852,036 filed Nov. 16, 1977, now abandoned.

STATE OF THE ART

French Pat. No. 1,450,375 describes cobamide derivatives having a different structural formula. Vitamin $B_{12}$ is known to play a very important role in humans on the rate of diverse biochemical processes requiring the presence of the said vitamin. It is also known that this vitamin is not active directly but is transformed by hepatic cells into a coenzyme of vitamin $B_{12}$, also known as dibencozide. The coenzyme of vitamin $B_{12}$ is particularly indispensible in humans since it favors and accelerates enzymatic reactions that control the synthesis of proteins, lipoproteins and nucleoproteins. When there is a dificiency of hepatic cells, it is desirable to orally or parenterally administer the coenzyme. Administration of dibencozide permits at most a blood level significantly superior to physiological levels only for a few hours at most and therefore dibencozide has to be administered repeatedly over a period of time. It is also known to attempt modifications of the galenic forms to try, without great success, to extend the time of activity of dibencozide and the most notable reason is the inherent weak stability of the molecule so that modifications can not be effected.

OBJECTS OF THE INVENTION

It is an object of the invention to provide novel cobamide derivatives of formula I and to a novel process for their preparation.

It is another object of the invention to provide novel compositions having protidic, anabolisant and antalgic activity and to provide a novel method of inducing protidic, anabolisant and antalgic activity in warm-blooded animals.

These and other objects and advantages of the invention will become obvious from the following detailed description.

THE INVENTION

The compounds of the invention have the formula:

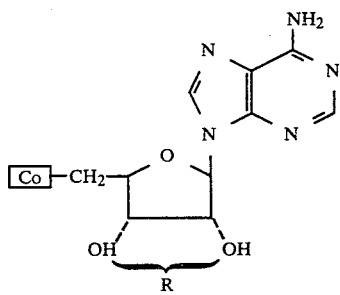

wherein R is acyl of an organic carboxylic acid of 4 to 20 carbon atoms and [Co] is α-(5,6-dimethyl-benzimidazolyl)-cobamide in the form of a mixture of monoesters as only one of the hydroxyl groups is esterified in each molecule. The novel products of formula I have kept the activity of the starting molecule, dibencozide, but present a more prolonged duration of activity which is due to the introduction of certain acyl groups into the purine moiety of dibencozide.

In the two earlier applications, the products of formula I of the invention were indicated as being amides as it was originally believed that the amino group was believed to be acylated but further analysis of the products has established that the compounds of formula I are a mixture of monoesters. A diester is not formed by the process.

Examples of suitable acyl groups of aliphatic carboxylic acids are butyryl, valeryl, pivaloyl, caproyl, capryloyl, capryl, lauroyl, myristoyl, palmitoyl, stearoyl and eicosanoyl. Especially preferred are acyl groups of aliphatic carboxylic acids of 14 to 18 carbon atoms and specific preferred compounds are O-palmitoyl-dibencozide, O-stearoyl-dibencozide, O-myristoyl-dibencozide and O-caproyl-dibencozide. The nomenclature used is that accepted by the IUPAC-IUB commission for biochemical nomenclature published in Archives of Biochemistry and Biophysics, Vol. 161 (1974), iii–xi.

The novel process of the invention for the preparation of a compound of formula I comprises reacting dibencozide of the formula:

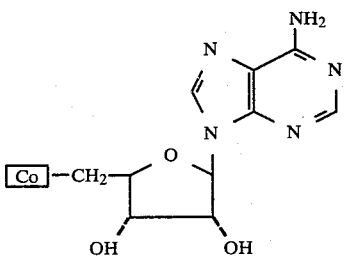

in the dark with a functional derivative of an acid of the formula:

R—OH    III wherein R and Co have the above definition.

Preferably, the functional derivative of the acid of formula III is the acid chloride, acid anhydride, mixed acid anhydride or a lower alkyl ester or sulfonate. The alkaline agent may be an alkali metal carbonate such as sodium carbonate or sodium bicarbonate and the reaction is effected in an aqueous organic solvent such as a water-dioxane mixture.

The reaction may also be effected under anhydrous conditions in the presence of a phenol such as phenol, m-cresol, p-cresol, o-cresol, m-methoxy-phenol or 4-tert.-butyl-2-methylphenol in an organic solvent such as chloroform, dichloromethane or dichloroethane.

The novel compositions of the invention having prolonged dibencozide properties are comprised of an effective amount of at least one compound of formula I and an inert pharmaceutical carrier or excipient. The compositions may be in the form of tablets, dragees, gelules, capsules, granules or injectable solutions or suspensions prepared in the known manner.

Examples of suitable excipients are talc, arabic gum, lactose, starch, magnesium stearate, aqueous or nonaqueous vehicles, fatty bodies of animal or vegetable origin, paraffinic derivatives, glycols, diverse wetting agents, dispersants or emulsifiers or preservatives.

The compositions are useful due to their protidic, anabolisant and antalgic properties which are presented in the blood at higher concentrations than physiological concentrations and as compared to dibencozide, the products of the invention have the advantage of assuring a larger and more elevated blood level. For example, subcutaneous administration of O-palmitoyl-dibencozide, O-myristoyl-dibencozide and O-stearoyl-dibencozide gives elevated blood levels for 12 to 24 hours thereafter while dibencozide administered under the same conditions does give less elevated levels for a shorter period of time.

The compositions are useful for the treatment of anorexia, of thinness, of hypothrepsia, growth retardation, asthenia with nursing infants and infants, for treatment of malnutrition states, of physic and psychic asthemia, of trophic troubles with the aged as well as for the treatment of rhumatismal pains and pains of diverse origins.

The preferred compositions of the invention have R as an acyl of 14 to 18 carbon atoms and the preferred compounds are O-stearoyl-dibencozide and O-palmitoyl-dibencozide when administered parenterally.

The novel method of the invention for inducing prolonged, elevated dibencozide activity in warm-blodded animals, including humans, comprises administering to warm-blooded animals a dibencozidally effective amount of at least one compound of formula I. The compounds may be administered orally, rectally or parenterally. For example, the compound of formula I may be intramuscularly administered at dose of 0.6 mg/kg one to 3 times a week in humans. The usual dose will vary from 0.02 to 0.6 mg/kg depending on the compound of the method of administration.

In the following examples there are described several preferred embodiments to illustrate the invention. However, it should be understood that the invention is not intended to be limited to the specific embodiments.

EXAMPLE 1

Coα-[α-(5,6-dimethylbenzimidazolyl)]-Coβ-O-palmitoyladenosylcobamide or O-palmitoyl-dibencozide The Example was effected in the darkness. A mixture of 1.58 g of dry dibencozide, 16 ml of an aqueous solution of 1.325% of sodium carbonate, 144 ml of water and 450 ml of dioxane was stirred until dissolution occured and 6.4 ml of a solution of 10% by volume of palmitoyl chloride in dioxane were added thereto with stirring twice at 30 minutes intervals. The mixture was stirred for 30 minutes and then another 16 ml of an aqueous solution of 1.325% sodium carbonate were added thereto followed by two additions of a solution of 10% palmitoyl chloride in dioxane at 30 minute intervals. The mixture was stirred at room temperature for about 68 hours and was concentrated to dryness under reduced pressure to obtain impure dry O-palmitoyl dibencozide.

The dry impure product was added to 158 ml of water and the aqueous solution was acidified to a pH of 5 with N sulfuric acid and was washed with ether. The pH of the aqueous solution was again adjusted to 5 and the aqueous phase was washed several times with ether. The pH of the aqueous phase was adjusted to 8.2 with sodium hydroxide solution and the aqueous phase was extracted several times with a 1–15 phenoldichloroethane mixture. The combined organic phases were washed with water to obtain 142 ml of the organic phase containing the desired product. The organic phase was added to 3 volumes of methyl ethyl ketone and one volume of water and the aqueous phase was recovered. The residual organic phase was extracted again with the lower phase of 1-3-1 dichloroethane-methyl ethyl ketone-water mixture and the aqueous phase was recovered. The combined aqueous phases were washed with the upper phase of a 1-3-1 dichloroethane-methyl ethyl ketone-water mixture and was evaporated to dryness under reduced pressure. The product was lyophilized to obtain 232 mg of O-palmitoyl-dibencozide in the form of a red-orange powder.

Analysis: $C_{88}H_{130}N_{18}O_{18}P$ Co; molecular weight = 1820; Calculated: %C: 58.07; %H: 7.2; %N: 13.9; Found: %C: 56.1; %H: 7.3; %N: 12.2.

EXAMPLE 2

O-caproyl-dibencozide or Coα-[α-5,6-dimethylbenzimidazolyl]-Coβ-O-caproyladenosylcobamide Again the Example was conducted in darkness. A mixture of 5 g of dry dibencozide, 50.6 ml of an aqueous solution of 1.325% sodium carbonate and 15.5 ml of a 10% solution of caproic acid anhydride in dioxane was stirred for 6 hours at room temperature and then another 15.5 ml of a 10% solution of caproic acid anhydride in dioxane was added thereto. The mixture was stirred for another 65 hours and was centrifuged. The recovered precipitated was dried under reduced pressure to obtain 5.28 g of raw product which was dissolved in 530 ml of a 1-7 phenol-dichloroethane mixture. The organic solution was washed with water to return the product to the aqueous phase by addition of 3 volumes of methyl ethyl ketone and one volume of water to obtain after lyophilization 940 mg of O-caproyl-dibencozide.

EXAMPLE 3

Coα-[5,6-dimethyl-benzimidazolyl)]-Coβ-O-myristoyl-adenosylcobamide or O-myristoyl-dibencozide Again the Example was effected in darkness. A mixture of 1.58 g of dry dibencozide, 32 ml of an aqueous solution of 1.325% sodium carbonate, 144 ml of distilled water and 320 ml of dioxane was stirred until dissolution occured and then 10.8 ml of a 10% volume solution of myristoyl chloride in dioxane were added thereto with stirring. The mixture was stirred for 15 minutes and then another 32 ml of an aqueous solution of 1.325% sodium carbonate and 10.8 ml of a solution of 10% by volume of myristoyl chloride in dioxane were added thereto. The mixture was stirred for 105 minutes and was concentrated under reduced pressure to obtain impure O-myristoyl-dibencozide in the form of a solution.

The solution was adjusted to a pH of 5 with N sulfuric acid and was then evaporated to dryness under reduced pressure. The residue was taken up in 158 ml of water and the pH was adjusted to 5. The aqueous phase was extracted with ether and was then adjusted a pH of 8.2 with N sodium hydroxide solution. The mixture was then extracted several times with a 1-15 phenol-dichloroethane mixture and the combined organic phases were washed with water to obtain 212 ml of the organic phase with the desired product. 3 volumes of methyl ethyl ketone and one volume of water were added to the organic phase and the aqueous phase was recovered. The organic phase was then treated with 132 ml of the lower phase of a 1-3-1 dichloroethane-methyl ethyl ketone-water mixture and the aqueous phase was recovered. The combined aqueous phases were washed with the upper phase of a 1-3-1 dichloroethane-methyl ethyl ketone-water mixture and were evaporated to dryness under reduced pressure. The residue was taken up in 500 ml of acetone and the mixture was vacuum filtered. The precipitate was dried under reduced pressure to obtain 687 mg of O-myristoyl-dibencozide in the form of a red powder.

Analysis: $C_{86}H_{128}N_{18}O_{18}PCo$; molecular weight=1790.3; Calculated: %C: 57.70; %H: 7.09; %N: 14.09; Found: %C: 57.4; %H: 7.2; %N: 13.1.

EXAMPLE 4

Coα-[α-(5,6-dimethyl-benzimidazolyl)]-Coβ-O-stearoyl-adenosylcobamide or O-stearoyl-dibencozide As in the previous example, the reaction was effected in darkness. A mixture of 1.58 g of dry bencozide, 32 ml of an aqueous solution of 1.325% sodium carbonate, 144 ml of distilled water and 320 ml of dioxane was stirred until dissolution occured and then 13.6 ml of a solution of 10% by volume of stearoyl chloride in dioxane were added thereto with stirring. The mixture was stirred for 15 minutes and another 32 ml of an aqueous solution of 1.325% sodium carbonate and 13.6 ml of a solution of 10% stearoyl chloride in dioxane were added thereto. The mixture was stirred for 105 minutes and was then concentrated under reduced pressure to obtain an impure solution of O-stearoyl-dibencozide.

The pH of the said solution was adjusted to 6.3 with N sulfuric acid and the solution was evaporated to dryness under reduced pressure. The residue was taken up in 158 ml of water and the pH was adjusted to 5 with 0.1 N sulfuric acid. The aqueous phase was washed several times with ether and its pH was then adjusted to 8.2 with sodium hydroxide solution. The mixture was then extracted several times with a 1-15 phenol-dichloroethane mixture and the combined organic phases were washed with water to obtain 161 ml of organic phase containing the desired product. The organic phase was washed with 3 volumes of methyl ethyl ketone and one volume of water and the aqueous phase was recovered. The organic phase was washed with 97 ml of lower phase of a 1-3-1 dichloroethane-methyl ethyl ketone-water mixture and the aqueous phase was recovered. The combined aqueous phases were then washed with the upper phase of the 1-3-1 dichloroethane-methyl ethyl ketone-water mixture and evaporated to dryness under reduced pressure. The residue was taken up in 500 ml of acetone and the mixture was vacuum filtered. The precipitate was dried to obtain 937.4 mg of O-stearoyl-dibencozide in the form of a red powder.

Analysis: $C_{90}H_{134}N_{18}O_{18}PCo$; molecular weight=1846.47; Calculated: %C: 58.56; %H: 7.32; %N: 13.66; Found: %C: 59.3; %H: 7.8; %N: 12.5.

EXAMPLE 5

Coα-[α-(5,6-dimethyl-benzimidazolyl)]-Coβ-O-palmitoyl-adenosylcobamide or O-palmitoyl-dibencozide 100 g of dry dibencozide were added at room temperature in the dark to 10 liters of a 1-10 phenol-chloroform mixture and after total dissolution occured, 100 g of palmitic acid anhydride were added thereto. The mixture was stirred for 6 hours and then another 100 g of palmitic acid anhydride were added thereto. The mixture was stirred for 16 hours at room temperature and was then washed 3 times with water. The organic phase was evaporated to dryness to obtain 47.44 g of residue which was treated with 10 liters of petroleum ether to remove any residual phenol and palmitic acid. The residue was added to one liter of acetone and the mixture was stirred for 30 minutes and was filtered. The recovered product was washed 3 times with 750 ml of acetone, was vacuum filtered and dried to obtain 49.34 g of O-palmitoyl-dibencozide in the form of a reddish-orange powder. The product was identical to that of Example 1.

EXAMPLE 6

O-palmitoyl-dibencozide 10 g of dry dibencozide were added at room temperature in the dark to one liter of a 1–10 p-cresol-chloroform mixture and after stirring the mixture for 30 minutes, 10 g of palmitic acid anhydride were added thereto. The mixture was stirred for 6 hours and then another 10 g of palmitic acid anhydride were added thereto the mixture was stirred for 16 hours and was then washed three times with water. The organic phase was evaporated to dryness under reduced pressure and the residue was dissolved in one liter of petroleum ether. The mixture was stirred at room temperature for 2 hours and the petroleum ether was decanted. The product was added to 250 ml of acetone and the mixture was stirred for one hour and allowed to stand overnight at room temperature. The mixture was vacuum filtered and the recovered product was washed 3 times with 20 ml of acetone and was vacuum filtered and dried to obtain 6.9 g of O-palmitoyl-dibencozide in the form of a reddish-orange powder. The product was identical to that of Example 1.

EXAMPLE 7

An injectable solution was prepared containing 10 mg of O-palmitoyl-dibencozide or O-stearoyl-dibencozide and 2 ml of sterile solvent which was prepared just before use.

PHARMACOLOGICAL DATA

Determination of blood levels in rats

Groups of rats received subcutaneously dibencozide or O-palmitoyl-dibencozide at a rate of 500 μg of dibencozide per kg of body weight and the blood levels were determined by bacteriological titration and expressed in ng of vitamin $B_{12}$ per ml of blood. Two series of tests were conducted and in each test, different groups of rats received an injection of an aqueous solution of dibencozide and an aqueous solution containing 10% ethanol of O-palmitoyl-dibencozide.

In the first test, samples were taken 1,3 and 6 hours after administration of the product and in the second test, samples were taken 1,3,6,16 and 24 hours after administration of the test product. At the end of each period considered and for each test product, 5 animals were killed and the blood levels were determined. The content of vitamin $B_{12}$ in the serum of untreated animals was 8.3 ng/ml. The results are reported in Table I.

TABLE I

| Test No. | after treatment | Content of Vitamin $B_{12}$ ng/ml | |
|---|---|---|---|
| | | dibencozide | O—palmitoyl-dibencozide |
| 1 | 1 | 455 ± 16 | 657 ± 69 |
| | 3 | 71 ± 7 | 1574 ± 161 |
| | 6 | 26 ± 5 | 1162 ± 77 |
| | 1 | 262 | 600 |

TABLE I-continued

| Test No. | after treatment | Content of Vitamin $B_{12}$ ng/ml | |
|---|---|---|---|
| | | dibencozide | O—palmitoyl-dibencozide |
| | 3 | 83 | 945 |
| 2 | 6 | 39 | 750 |
| | 16 | 13 | 193 |
| | 24 | 8 | 64 |

The test was repeated again with all the test products being administered in aqueous solution containing 10% ethanol and samples were taken 1,3,6,16 and 24 hours after administration of the test products and the results are reported in Table II.

TABLE II

| Time in Hours | Level of Vitamin $B_{12}$ in ng/ml | | | |
|---|---|---|---|---|
| | Dibencozide | O—palmitoyl Dibencozide | O—myristoyl Dibencozide | O—stearoyl Dibencozide |
| 1 | 474 ± 9 | 820 ± 55 | 471 ± 59 | 494 ± 67 |
| 3 | 130 ± 12 | 1333 ± 58 | 823 ± 85 | 910 ± 41 |
| 6 | 49 ± 4 | 880 ± 36 | 404 ± 19 | 453 ± 37 |
| 16 | 28.8 ± 8 | 221 ± 7 | 117 ± 4 | 273 ± 60 |
| 24 | 34 ± 0 | 88 ± 4 | 56 ± 6 | 140 ± 7 |

The results of Tables I and II show that the tested compounds of the invention at the same dose as dibencozide exert a greater and more prolonged activity then dibencozide.

Various modifications of the products and methods of the invention may be made without departing from the spirit or scope thereof and it is to be understood that the invention is intended to be limited only as defined in the appended claims.

We claim:

1. A compound of the formula:

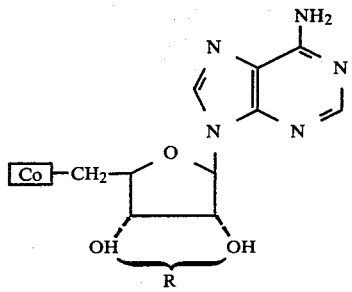

wherein R is acyl of an aliphatic carboxylic acid of 4 to 20 carbon atoms and [Co] is α-(5,6-dimethyl-benzimidazolyl)-cobamide.

2. A compound of claim 1 wherein R is acyl of an aliphatic carboxylic acid of 14 to 18 carbon atoms.

3. A compound of claim 1 which is O-palmitoyl-dibencozide.

4. A compound of claim 1 which is O-stearoyl dibencozide.

5. A compound of claim 1 which is O-myristoyl-dibencozide.

6. A compound of claim 1 which is O-caproyl-debencozide.

7. A composition with prolonged and elevated dibencozide activity comprising a dibencozidally effective amount of at least one compound of claim 1 and an inert pharmaceutical carrier.

8. A composition of claim 7 wherein the compound is O-palmitoyl-dibencozide.

9. A composition of claim 7 wherein the compound is O-myristoyl-dibencozide.

10. A composition of claim 7 wherein the compound is O-stearoyl-dibencozide.

11. A method of inducing prolonged and elevated dibencozide activity in warm-blooded animals comprising administering to warm-blooded animals an amount of at least one compound of claim 1 sufficient to induce prolonged and elevated dibencozide activity.

12. The method of claim 11 wherein the compound is O-palmitoyl-dibencozide.

13. The method of claim 11 wherein the compound is O-myristoyl-dibencozide.

14. The method of claim 11 wherein the compound is O-stearoyl-dibencozide.

* * * * *